United States Patent
E.M. Jaillon et al.

(10) Patent No.: US 10,154,784 B2
(45) Date of Patent: Dec. 18, 2018

(54) SPEED MEASURING DEVICE, SPEED MEASURING METHOD, AND RECORDING MEDIUM

(71) Applicant: TOMEY CORPORATION, Nagoya-shi, Aichi (JP)

(72) Inventors: Franck E.M. Jaillon, Nagoya (JP); Naoko Hara, Nagoya (JP); Tsutomu Ohmori, Nagoya (JP)

(73) Assignee: TOMEY CORPORATION, Nagoya-shi, Aichi (JP)

( * ) Notice: Subject to any disclaimer, the term of this patent is extended or adjusted under 35 U.S.C. 154(b) by 334 days.

(21) Appl. No.: 15/176,825

(22) Filed: Jun. 8, 2016

(65) Prior Publication Data
US 2017/0038403 A1    Feb. 9, 2017

(30) Foreign Application Priority Data

Jun. 8, 2015   (JP) .................................. 2015-115881
May 23, 2016  (JP) .................................. 2016-102627

(51) Int. Cl.
| | |
|---|---|
| *A61B 3/12* | (2006.01) |
| *G01P 3/68* | (2006.01) |
| *A61B 3/10* | (2006.01) |
| *G01P 5/00* | (2006.01) |
| *G01P 5/18* | (2006.01) |
| *G01P 5/26* | (2006.01) |

(52) U.S. Cl.
CPC ............ *A61B 3/1233* (2013.01); *A61B 3/102* (2013.01); *G01P 3/68* (2013.01); *G01P 5/00* (2013.01); *G01P 5/18* (2013.01); *G01P 5/26* (2013.01)

(58) Field of Classification Search
CPC ......... A61B 3/102; A61B 3/1233; G01P 3/68; G01P 5/00; G01P 5/18; G01P 5/26
See application file for complete search history.

(56) References Cited

U.S. PATENT DOCUMENTS

| | | | |
|---|---|---|---|
| 7,995,814 B2* | 8/2011 | Fingler | A61B 3/102 378/4 |
| 9,492,082 B2* | 11/2016 | Yoshida | A61B 5/0066 |
| 2010/0259698 A1 | 10/2010 | Powers et al. | |
| 2012/0053904 A1 | 3/2012 | Yuasa et al. | |

FOREIGN PATENT DOCUMENTS

JP        2010259698 A    11/2010

\* cited by examiner

*Primary Examiner* — Eric L Bolda
(74) *Attorney, Agent, or Firm* — David D. Brush; Westman, Champlin & Koehler, P.A.

(57) ABSTRACT

A speed measuring device with an optical coherence tomography is provided. The speed measuring device includes an optical coherence tomography that obtains an tomographic image of a sample, a motion contrast calculator, a waveform creator that creates a motion contrast wave indicating chronological change of motion contrast, a time lag calculator, a distance calculator that calculates the blood vessel distance in a sample, and a speed calculator that calculates speed of a pulse wave transmitted inside the blood vessel.

11 Claims, 10 Drawing Sheets

SPEED MEASURING DEVICE, SPEED MEASURING METHOD, AND RECORDING MEDIUM

CROSS-REFERENCE TO RELATED APPLICATIONS

This application claims the benefit of Japanese Patent Applications No. 2015-115881 filed on Jun. 8, 2015 and No. 2016-102627 filed on May 23, 2016 with the Japan Patent Office, the entire content of the Japanese Patent Application No. 2015-115881 and the Japanese Patent Application No. 2016-102627 are incorporated herein by reference.

BACKGROUND

The present disclosure relates to a speed measuring device with an optical coherence tomography and a method of measuring speed.

As disclosed in the publication of the Japanese Unexamined Patent Application Publication No. 2010-259698, a technique is known in optical coherence tomography in which moving speed of inspection target is measured based on the amount of chronological change in the phase of an interference signal.

SUMMARY

In the aforementioned technique, there has been a problem in that as the angle formed by the incident direction of light emitted on an inspection target and the moving direction of the inspection target becomes closer to 90 degrees, the measuring accuracy of moving speed deteriorates.

In one aspect of the present disclosure, the accuracy in speed measurement with an optical coherence tomography is desirably improved.

A speed measuring device according to one aspect of the present disclosure comprises an optical coherence tomography, a motion contrast calculator, a waveform creator, a time lag calculator, a distance calculator, and a speed calculator.

The optical coherence tomography divides light, emitted from a light source, into reference light and measuring light to emit the measuring light to irradiation points, which are different from each other, on a surface of a sample including a blood vessel, and to obtain a tomographic image of the sample based on one or more interference signal(s) in which one or more reflected light(s), obtained from the measuring light reflected on the sample, and the reference light are interfering.

The motion contrast calculator continuously calculates one or more first motion contrast(s) and one or more second motion contrast(s). Among the irradiation points, one irradiation point disposed on the blood vessel is defined as a first irradiation point, and another irradiation point disposed on the blood vessel, passes through the first irradiation point, and is different from the first irradiation point is defined as a second irradiation point, and the one or more first motion contrast(s) is/are one or more motion contrast(s) calculated based on the one or more interference signal(s) at the first irradiation point, and the one or more second motion contrast(s) is/are the one or more motion contrast(s) calculated based on the one or more interference signal(s) at the second irradiation point.

The waveform creator creates, based on a calculation result obtained by the motion contrast calculator, a first motion contrast waveform, indicating chronological change in the one or more first motion contrast(s), and a second motion contrast waveform, indicating a chronological change in the one or more second motion contrast(s).

The time lag calculator calculates time lag that is temporal lag between the first motion contrast waveform and the second motion contrast waveform created by the waveform creator.

The distance calculator calculates a blood vessel distance along the blood vessel from the first irradiation point to the second irradiation point.

The speed calculator that calculates, based on the time lag calculated by the time lag calculator and the blood vessel distance calculated by the distance calculator, pulse wave velocity that is velocity of a pulse wave transmitted inside the blood vessel.

The speed measuring device configured as above continuously calculates the one or more first and the second motion contrast waveforms at the first and the second irradiation points disposed on the blood vessel so as to create the first and the second motion contrasts. Accordingly, the speed measuring device can obtain movement of pulse waves at the first irradiation point and the second irradiation point disposed on the blood vessel.

Then, the speed measuring device calculates, based on the time lag of the first and the second motion contrast waveforms, and the aforementioned blood vessel distance, the pulse wave velocity that is the velocity of a pulse wave transmitted inside the blood vessel. Accordingly, the speed measuring device does not need to use the angle formed by the incident direction of the measuring light and the moving direction of the blood inside the blood vessel to measure the pulse wave velocity. This prevents reduction in the accuracy in the moving speed irrespective of the angle formed by incident direction of the measuring light and moving direction of blood being nearly 90 degrees, and the speed measuring device can have the accuracy in speed measurement improved. Moreover, since the speed measuring device can capture the movement of a pulse wave itself, the speed measuring device is unlikely to be affected by local turbulent and so on.

Moreover, in the speed measuring device, the one or more motion contrast(s) may include(s), specifically, information indicating a phase difference between two interference signals calculated at different time from each other, or may include(s) information indicating an amplitude difference between two interference signals calculated at different time from each other.

Moreover, in the speed measuring device, the optical coherence tomography may scan the measuring light on a surface of the sample along the blood vessel that passes through the first irradiation point and the second irradiation point.

This allows the speed measuring device to increase the number of the irradiation positions on a surface of the sample along the blood vessel. As the number of the irradiation positions increases on the blood vessel, a motion contrast waveform can be calculated at every narrow interval along the blood vessel, which enables the speed measuring device to accurately calculate local pulse wave velocity.

Moreover, in the speed measuring device, the optical coherence tomography may perform first scan and second scan on a surface of the sample, in the first scan, the measuring light scanning in a circular manner so as to intersect with the first irradiation point, and in the second scan, the measuring light scanning in a circular manner so as to intersect with the second irradiation point and to include a scan area of the first scan.

This allows the speed measuring device to measure the pulse wave velocity of a blood vessel that intersects with the circle of the first scan at the first irradiation point and with the circle of the second scan at the second irradiation point. Moreover, the speed measuring device can calculate the one or more motion contrast at irradiation points other than the first irradiation point in the circle of the first scan and the second irradiation point in the circle of the second scan. Accordingly, the speed measuring device can measure the speed of pulse waves of blood vessels intersecting with both of the circle of the first scan and the circle of the second scan.

In a case in which the aforementioned first scan and the second scan are performed, in the speed measuring device, the motion contrast calculator calculates the one or more the first motion contrast(s) and the one or more the second motion contrast(s), among the irradiation points, an irradiation point irradiated by the first scan being defined as the first irradiation point, and an irradiation point irradiated by the second scan being defined as the second irradiation point. In the speed measuring device, the time lag calculator may calculate the time lag based on a difference between time from when a pulse or a pulse wave is detected until when a preset comparison part of the first motion contrast waveform is detected (to be referred to as first detection time hereinafter), and time from when a pulse or a pulse wave is detected until when the comparison part of the second motion contrast waveform is detected (to be referred to as second detection time hereinafter).

The first motion contrast waveform and the second motion contrast waveform might have captured pulse waves that are different from each other. However, under the condition that the blood flow speed does not significantly change at every pulse, in a case in which different pulse waves are captured, the difference between the first detection time and the second detection time is substantially equivalent to the difference in a case in which an identical pulse wave is captured in the first motion contrast pulse form and the second motion contrast pulse form.

Moreover, the speed measuring device comprises an inner radius calculator and a blood flow amount calculator.

The inner radius calculator calculates an inner radius of the blood vessel based on the one or more interference signal(s) obtained by the optical coherence tomography. The blood flow amount calculator calculates a blood flow amount of the blood vessel based on the inner radius calculated by the inner radius calculator and the pulse wave velocity calculated by the speed calculator.

This allows the speed measuring device to calculate not only the pulse wave velocity of a blood vessel but also the blood flow amount of the blood vessel.

Furthermore, the speed measuring device comprises an outer and inner radii calculator and an elasticity calculator.

The outer and inner radii calculator calculates an outer radius and an inner radius of the blood vessel based on the one or more interference signal(s) obtained by the optical coherence tomography. The elasticity calculator calculates blood vessel elasticity of the blood vessel based on the outer radius and the inner radius calculated by the outer and inner radii calculator and the pulse wave velocity calculated by the speed calculator.

This allows the speed measuring device to calculate not only the pulse wave velocity of a blood vessel but also the elasticity of a blood vessel.

Moreover, the speed measuring device, if the sample is a retina, the positions of the first irradiation point and the second irradiation point are preferably set such that the blood vessel distance is extended by 0.15 mm. This allows, if the sample is a retina, the speed measuring device to prevent an increase of the calculation error of the transmission time Tp, and, therefore, prevents the reduction in the detection accuracy in the pulse wave speed.

A speed measuring program according to one aspect of the present disclosure makes a computer function as each means of a speed measuring device. Moreover, the speed measuring program may be recorded in a recording medium and provided.

The computer controlled by the speed measuring program can construct one portion of the speed measuring device, and with the computer, the same effect as the effect of the speed measuring device can be achieved.

The speed measuring method according to one aspect of the present disclosure uses an optical coherence tomography that divides light, emitted from a light source, into reference light and measuring light to emit the measuring light to irradiation points, which are different from each other, on a surface of a sample including a blood vessel, and to obtain a tomographic image of the sample based on one or more interference signal(s) in which one or more reflected light(s), obtained from the measuring light reflected on the sample, and the reference light are interfering.

The speed measuring method comprises a motion contrast calculation procedure, a waveform creating procedure, a time lag calculation procedure, a distance calculation procedure, and a speed calculation procedure.

In the motion contrast calculation procedure, one or more first motion contrast(s) and one or more second motion contrast(s) are continuously calculated. Among the irradiation points, one irradiation point disposed on the blood vessel is defined as a first irradiation point, and another irradiation point that is disposed on the blood vessel, passes through the first irradiation point, and is different from the first irradiation point is defined as a second irradiation point. Furthermore, the one or more first motion contrast(s) is/are one or more motion contrast(s) calculated based on the one or more interference signal(s) at the first irradiation point, and the one or more second motion contrast(s) is/are the one or more motion contrast(s) calculated based on the one or more interference signal(s) at the second irradiation point.

In the waveform creating procedure, based on a calculation result obtained by the motion contrast calculator, a first motion contrast waveform, indicating chronological change in the one or more first motion contrast(s), and a second motion contrast waveform, indicating a chronological change in the one or more second motion contrast(s) are created.

In the time lag calculating procedure, time lag that is temporal lag between the first motion contrast waveform and the second motion contrast waveform created by the waveform creator are calculated.

In the distance calculating procedure, a blood vessel distance along the blood vessel from the first irradiation point to the second irradiation point is calculated.

In the speed calculating procedure, based on the time lag calculated by the time lag calculator and the blood vessel distance calculated by the distance calculator, pulse wave velocity is calculated.

The speed measuring method is a method executed in the speed measuring device, by executing the method, the same effect as the effect of the speed measuring device can be achieved.

BRIEF DESCRIPTION OF THE DRAWINGS

The present invention will now be described by way of example with reference to the accompanying drawings, in which:

FIGS. 3A-3B are diagrams in which FIG. 3A shows a measuring area in a retinal image, and FIG. 3B shows an axis of a blood vessel and a line parallel to the axis;

FIGS. 4A-4B are a perspective view and a graph in which FIG. 4A shows a blood vessel BV1 and FIG. 4B shows pulse wave maps PW1 and PW2;

DETAILED DESCRIPTION OF THE PREFERRED EMBODIMENTS

Figure 1:
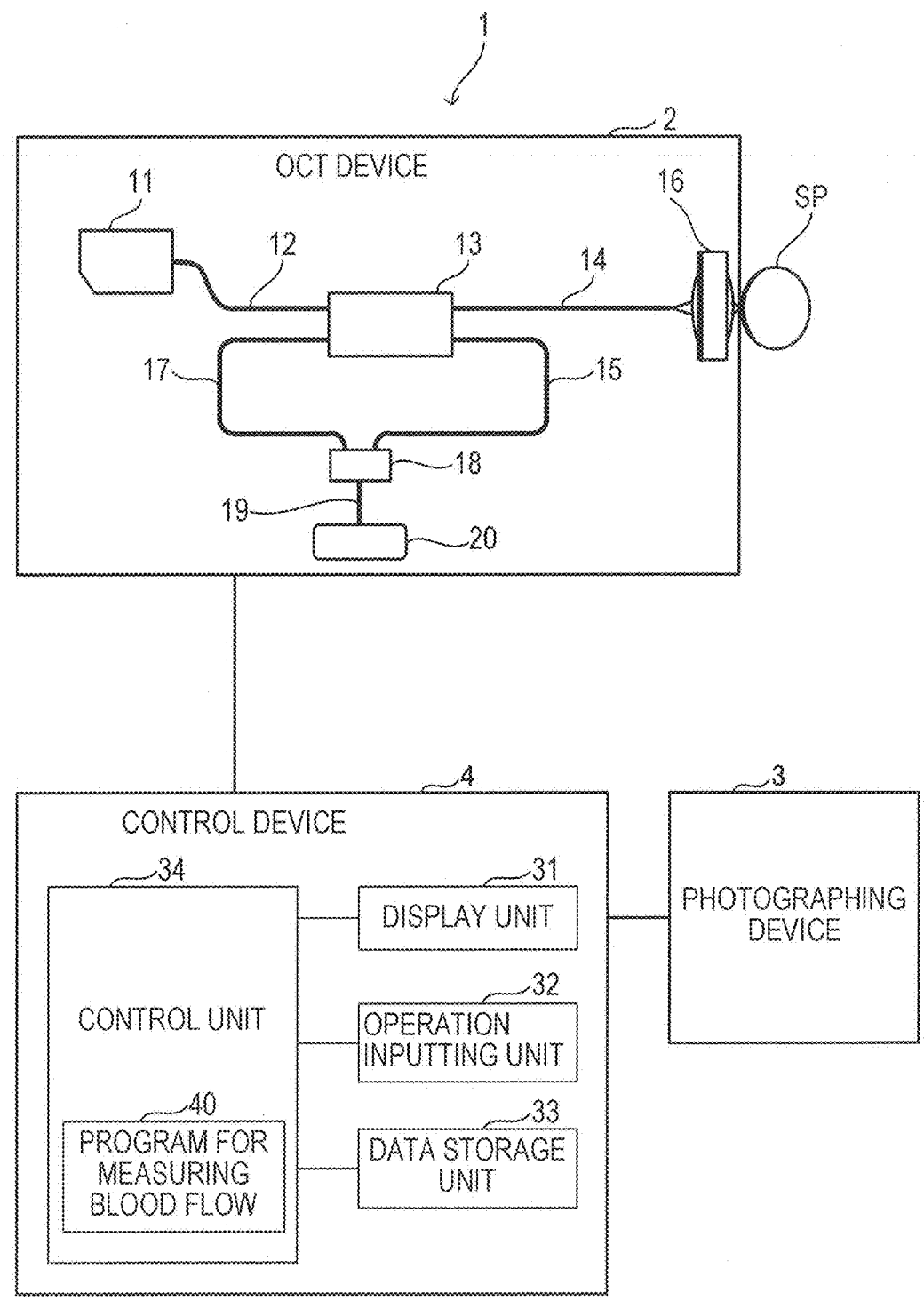
FIG. 1 is a diagram showing the configuration of a blood flow measuring device.

A blood flow measuring device 1 according to the present embodiment comprises, as shown in FIG. 1, an Optical Coherence Tomography (OCT: Optical Coherence Tomography) device 2 (to be referred to as OCT device 2, hereinafter), a photographing device 3, and a control device 4.

The OCT device 2 is a device that utilizes optical coherence to take two-dimensional tomographic images of samples, and is Swept Source OCT (SS-OCT: Swept Source OCT) in the present embodiment.

The OCT device 2 comprises a light source 11, an optical fiber 12, a fiber coupler 13, a measuring arm 14, a reference arm 15, a scanner 16, an optical fiber 17, a fiber coupler 18, an optical fiber 19, and a detector 20.

The light source 11 is a swept source light source, and generates wide-band light.

The optical fiber 12 is a light transmission path connecting the light source 11 and the fiber coupler 13, and transmits the light outputted from the light source 11 to the fiber coupler 13.

The fiber coupler 13 divides the light inputted from the light source 11 through the optical fiber 12 into reference light and measuring light.

The measuring arm 14 is a light transmission path connecting the fiber coupler 13 and the scanner 16. The measuring arm 14 transmits measuring light outputted from the fiber coupler 13 to the scanner 16, and the reflected light outputted from the scanner 16 to the fiber coupler 13.

The reference arm 15 is a light transmission path connecting the fiber coupler 13 and the fiber coupler 18, and transmits the reference light outputted from the fiber coupler 13 to the fiber coupler 18.

The scanner 16 performs two-dimensional scan by directing the light, inputted through the measuring arm 14, onto a sample SP (a retina of a subject in the present embodiment), and outputs the light reflected on the sample SP to the measuring arm 14. The scanner 16 has functions to adjust the length of the measuring arm 14, the optical magnification and the focus.

Moreover, the fiber coupler 13 outputs the light inputted from the scanner 16 through the measuring arm 14 to the optical fiber 17.

The optical fiber 17 is a light transmission path connecting the fiber coupler 13 and the fiber coupler 18, and transmits the light outputted from the fiber coupler 13 to the fiber coupler 18.

The fiber coupler 18 outputs light that is a combination of the reference light, inputted through the reference arm 15, and the reflected light, inputted through the optical fiber 17 (to be referred to as an interference signal hereinafter). The interference signal is composed of an amplitude and a phase.

The optical fiber 19 is a light transmission path connecting the fiber coupler 18 and a detector 20 and transmits the interference signal outputted from the fiber coupler 18 to the detector 20.

The detector 20 detects the interference signal inputted from the fiber coupler 18 through the optical fiber 19.

A photographing device 3 takes images of a sample SP (an en-face view of a retina of a subject in the present embodiment) and outputs the photographic data indicating the photographic image to the control device 4.

The control device 4 comprises a display unit 31, an operation inputting unit 32, a data storage unit 33, and a control unit 34.

The display unit 31 comprises a display device (not shown) and shows various images on a screen of the display device.

The operation inputting unit 32 outputs input operation information that specifies input operation performed by a user with a keyboard (not shown) and/or a mouse (not shown).

The data storage unit 33 is a memory device that stores various data.

The control unit 34 executes various processes based on the input from the OCT device 2, the photographing device 3, and the operation inputting unit 32 and controls the OCT device 2, the photographing device 3, the display unit 31, and the data storage unit 33.

In the blood flow measuring device 1 configured as above, the control unit 34 executes a process for measuring blood flow.

Figure 3A:
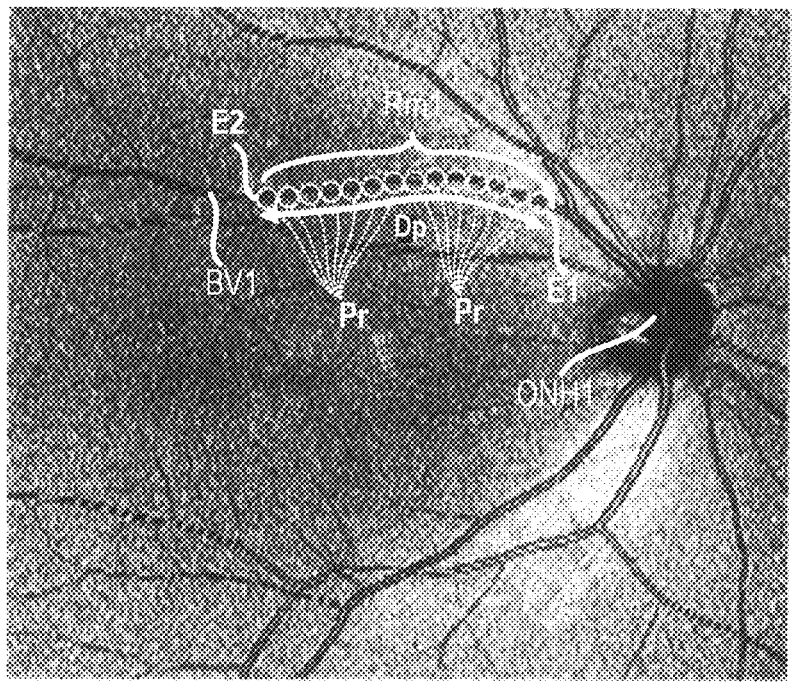

The following describes the procedure of the process for measuring blood flow executed by the control unit 34. The process for measuring blood flow is executed when the following three conditions are met:

1) the image of the eye fundus of the sample SP taken by the photographing device 3 is shown on the screen of the display unit 31 (see FIG. 3A);

2) light scan to take a two-dimensional tomographic image (to be referred to as scanning for a tomographic image hereinafter) has been performed by the OCT device 2; and 3) a program for measuring blood flow 40, stored in the control unit 34 to perform the process for measuring blood flow, is started by a user's input operation.

The program for measuring blood flow 40 may be pre-installed in the blood flow measuring device 1 or may be installed through a recording medium or a network. Moreover, the program for measuring blood flow 40 may be recorded in a recording medium and provided to users. The recording medium may be "non-transitory tangible storage media (non-transitory tangible storage media) such as, for example, optical disks, magnetic disks, and semiconductor memories.

Figure 2A:
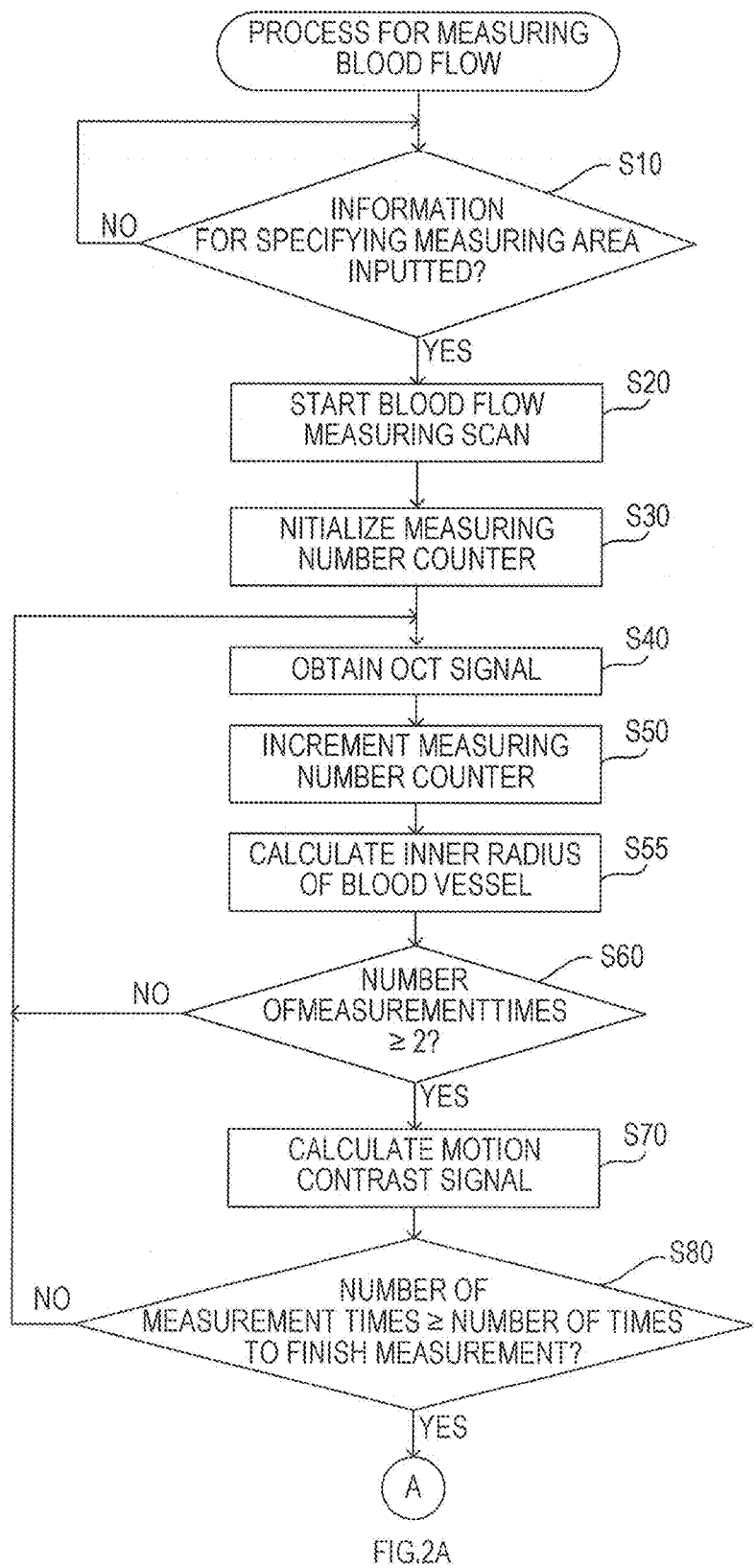
FIGS. 2A-2B are flowcharts showing a process for measuring blood flow.
Figure 2B:
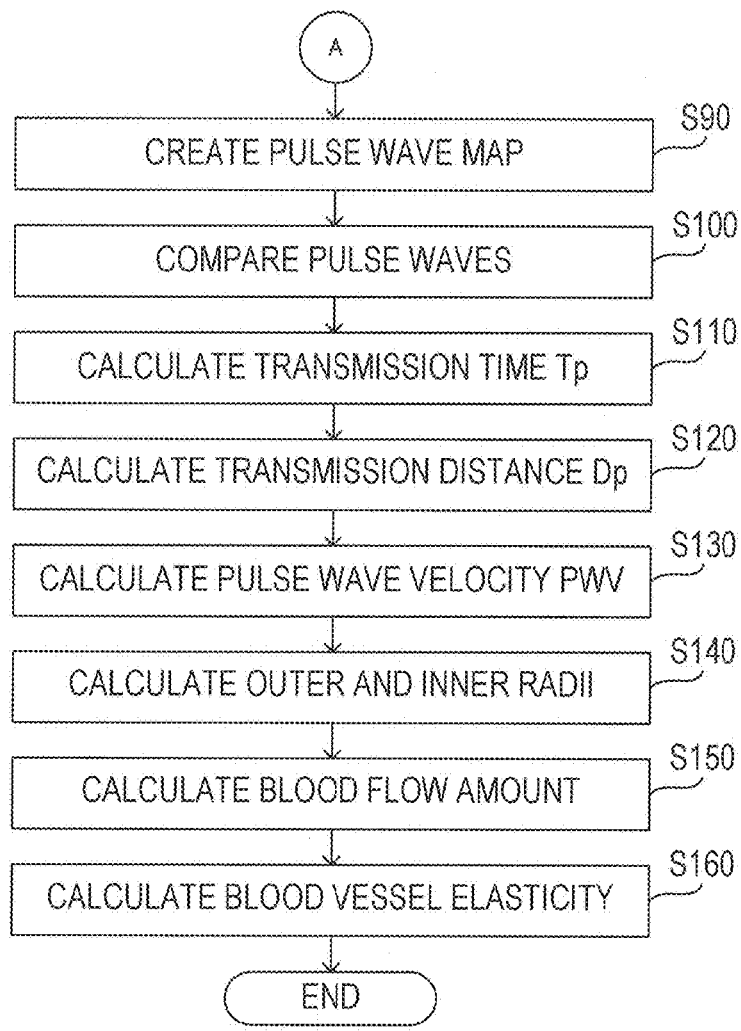

When the process for measuring blood flow is executed, the control unit 34, as shown in FIGS. 2A and 2B, initially determines, in S10, whether or not information for specifying the measuring area, which specifies, in the image of the eye fundus of sample SP shown on the display unit 31, the measuring area selected by a user, has been inputted from the operation inputting unit 32. In S10, as shown in, for example, FIG. 3A, a portion Rm1 located along a blood vessel BV1 in vicinity of an optic disc ONH1 is set to the measuring area.

If it is determined that no information for specifying the measuring area has been inputted (S10: NO), the control unit 34 waits until information for specifying the measuring area is inputted (repeats the process of S10). When information for specifying the measuring area is inputted (S10: YES), in S20, the control unit 34 enables the OCT device 2 to start blood flow measuring scan. Consequently, the OCT device 2 switches the scanning of measuring light, performed by the scanner 16, from tomographic image scanning to the blood flow measuring scan. Specifically, in the blood flow measuring scan, light is sequentially emitted (see measuring points Pr in FIG. 3) from one end of measuring area (see one end E1 in FIG. 3A), which is specified by the information for specifying the measuring area, along the blood vessel toward the other end (see other end E2 in FIG. 3A) to detect an interference signal corresponding to each of the measuring points. During the execution of the blood flow measuring scan, eye-tracking is performed so as to avoid a motion artifact. A motion artifact is image noise that appears due to random movement of a measuring area (a retina of a subject). Eye-tracking is a process to identify the position of the eye fundus of an eye of a subject. The measurement of distance along a blood vessel is dependent on the axial length of the eye.

In the blood flow measuring scan, two-dimensional scan, in which light scans from one end to the other end of the measuring area, is performed at every preset measuring interval $\Delta t$. The two-dimensional scan is performed a preset number of times to finish measurement. Then, the blood flow measuring scan finishes. Once the blood flow measuring scan finishes, the OCT device 2 automatically switches the scanning of the measuring light, performed by the scanner 16, from the blood flow measuring scan to the tomographic image scanning.

The blood flow measuring scan is started in S20, and subsequently in S30, a measuring number counter provided to the control unit 34 is initialized (set to zero). Then, in S40, interference signals detected in the latest two-dimensional scan at each of the measuring points are obtained as OCT signals OCT (s, z, ti) from the OCT device 2 (i=1, 2, 3, . . . ).

The variable s in the OCT (s, z, ti) indicates the position of a measuring point in the curvilinear coordinate along the blood vessel in the measuring area.

Figure 3B:
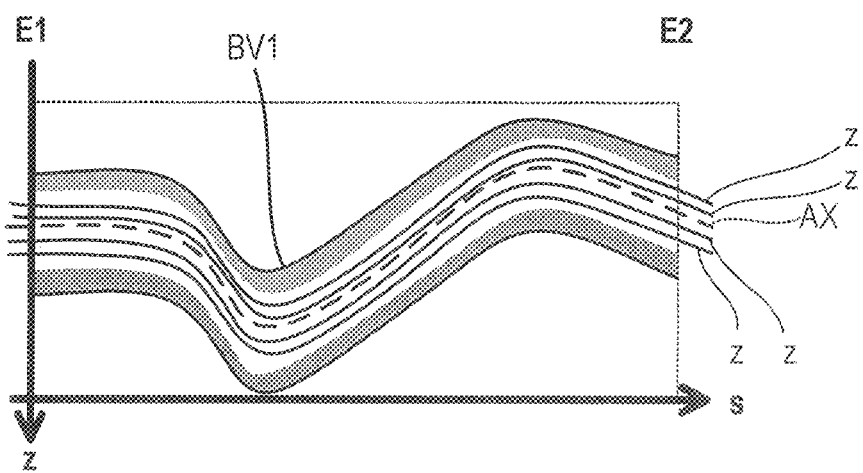

The variable z is a variable to specify a plurality of lines (see the axially-parallel line z in FIG. 3(B)) that are parallel to the blood vessel axis AX of a blood vessel in the measuring area. That is, the variable z indicates the position along the vertical line to the blood vessel axis AX in the blood vessel.

The variable ti indicates the timing at which two-dimensional scan is performed.

For example, OCT methods that are highly accurate with respect to movement exist, such as amplitude decorrelation (amplitude decorrelation) or speckle decorrelation (speckle decorrelation). Moreover, information on pulse waves can be obtained by monitoring the chronological change in the diameter of a blood vessel.

Subsequently in S50, the measuring number counter is incremented (one added). Next, in S55, based on the OCT signals obtained in S40, the inner radius r1 (ti) of the blood vessel in one end E1 and the inner radius r2 (ti) of blood vessel of the other end E2 are calculated. In S60, it is determined whether or not the value of the measuring number counter (hereinafter, to be also referred to as measuring number) is two or more.

If it is determined here that the measuring number is less than two (S60: NO), the process goes to S40. On the other hand, if it is determined that the measuring number is two or more (S60: YES), in S70, a motion contrast signal M (s, z, ti) is calculated.

The motion contrast signal M (s, z, ti) is calculated with the following formula (1), in which $\Phi$(s, z, ti) is a phase of an OCT signal OCT (s, z, ti).

$$M(s,z,ti)=\Phi(s,z,ti+1)-\Phi(s,z,ti) \quad (1)$$

The phase difference $\Delta\Phi$ of an OCT signal caused by the movement between the measuring intervals $\Delta t$ is dependent on the direction of the incident light emitted onto a sample, and the direction of the movement of the incident light inside the sample. In a case in which the incident light is emitted along the direction of the z axis, the phase difference $\Delta\Phi$ to be detected varies corresponding to the z-axis directional component of the movement of the incident light inside the sample.

If the z-axis directional component of the speed of the particles of incident light moving inside the sample is represented as vz, the phase difference $\Delta\Phi$ is expressed in the following formula (2), in which $\lambda$ is the wave length of the incident light inside the sample.

$$\Delta\Phi=1\pi \times vz \times \Delta t/\lambda \quad (2)$$

Figure 4A:
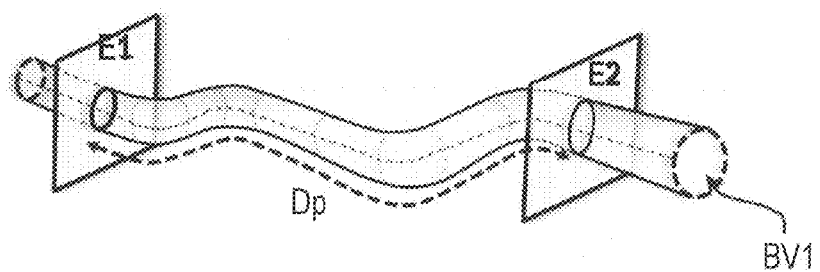
Figure 4B:
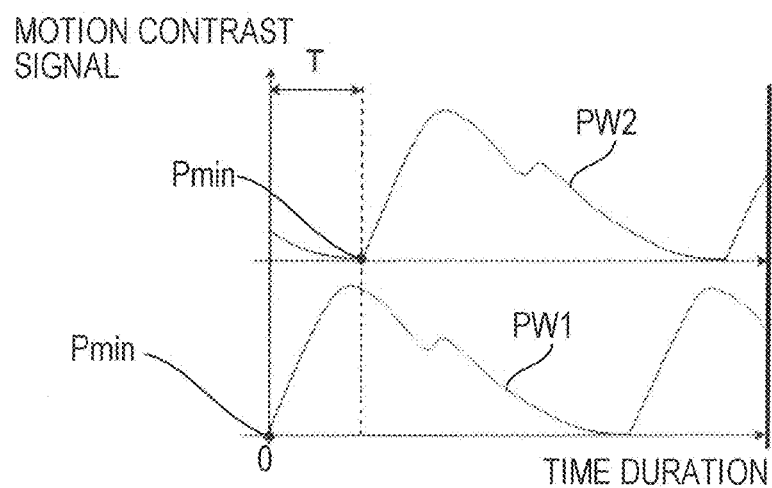

Then in S80, it is determined whether or not the value of the measuring number counter (measuring number) is the aforementioned number of times to finish measurement or more. If it is determined that the measuring number is less than the number of times to finish measurement (S80: NO), the process goes to S40. On the other hand, if it is determined that the measuring number is the number of times to finish measurement or more (S80: YES), in S90, with (the number of times to finish measurement−1) motion contrast signals M (s, z, ti) calculated at each of the measuring points, pulse wave maps PW(s, z, t) indicating the chronological change of the motion contrast signals M (s, z, ti) are created for each of the measuring points. Pulse wave maps of a case as shown in, for example, FIG. 4A are shown in FIG. 4B in which blood flows inside the blood vessel BV1 from one end E1 toward the other end E2. FIG. 4B shows the pulse wave map PW1 at one end E1 and the pulse wave map PW2 at the other end E2.

Figure 5:
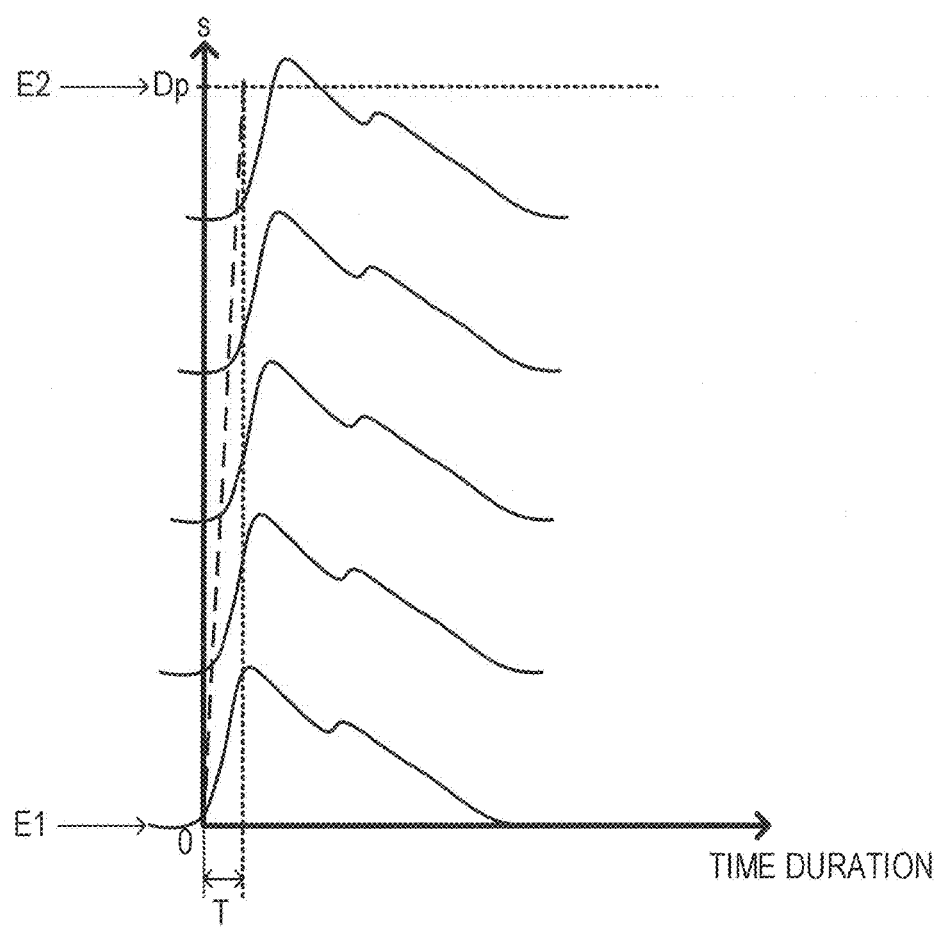
FIG. 5 is a graph showing a pulse wave map PW (s, z0, t)

FIG. 5 shows pulse wave maps PW(s, z0, t) created for a plurality of measuring points on one axially-parallel line z0 among a plurality of axially-parallel lines z.

FIG. 5 shows that pulse waves are transmitted along the axially-parallel line z0 from one end E1 to the other end E2, and that it takes transmission time t for the pulse waves to reach the other end E2 from one end E1.

When creating a pulse wave map finishes in S90, in S100, pulse wave maps created at each measuring point within the measuring area are compared to each other, and specifies comparison parts that have identical shapes. The method of comparison includes, for example, differentiation, integration or correlation of pulse waveforms. Moreover, the comparison parts include, for example, the part where the level of a pulse wave becomes the maximum, or the part where the level of a pulse wave becomes the minimum (see the minimum point Pmin in FIG. 4B).

Then in S110, based on the comparison result obtained in S100, the transmission time Tp is calculated. Specifically, for each of the pulse wave maps PW(s, z, t) at two measuring points, time t in the comparison part specified in S100 is determined. For example, as shown in FIG. 4B, in the pulse wave map PW1 that is the pulse wave map PW (0, z, t) at one end E1, the time t at the minimum point Pmin, specified as a comparison part, is 0. Moreover, in the pulse wave map PW2 that is the pulse wave map PW (d, z, t) at the other end E2, the time t at the minimum point Pmin, specified as a comparison part, is T.

Then, the time difference at the comparison part in the pulse wave maps PW(s, z, t) of the two measuring points is calculated as transmission time. For example, in FIG. 4B, T (=T−0) is obtained as the transmission time Tp. However, between the measuring points adjacent to each other, time lag exists that is dependent on a finite speed for scanning light. Accordingly, in the calculation for the transmission time Tp, correction is performed to consider this time lag.

In S110, the transmission time Tp is calculated with respect to axially-parallel lines z. Hereinafter, the transmission time Tp that corresponds to the axially-parallel line z is to be represented as Tp(z). Moreover, in S110, the arithmetic mean of the transmission time Tp (z) calculated with respect to the axially-parallel lines z is calculated as transmission time Tp.

Furthermore, in 8120, for each of axially-parallel lines z, the transmission distance Dp between two measuring points along the axially-parallel line z is calculated. Hereinafter, the transmission distance Dp of the axially-parallel line z is to be represented as Dp (z). Moreover, in S120, the arithmetic mean of the transmission distances Dp (z) calculated with respect to the axially-parallel lines z is calculated as the transmission distance Dp.

Subsequently, in S130, pulse wave velocity PWV is calculated. Specifically, for each of the axially-parallel lines z, Dp (z)/Tp (z) is first calculated as pulse wave velocity PWV (z). Then, the arithmetic mean of the pulse wave velocity PWV (z) calculated for the axially-parallel lines z is calculated as the pulse wave velocity PWV.

The artery pulse wave velocity in general is approximately 10 to 600 mm/s. For example, in a case in which the distance between one end E1 and the other end E2 is 1 mm and the artery pulse wave velocity is 100 mm/s, the transmission time Tp is 0.01 s.

To be exact, the pulse wave velocity PWV (z) is dependent on the variable z (z: depth). However, in the case of, for example, a retinal blood vessel, the direction of a blood vessel separating from the optic disc is generally vertical to incident light and the influence of the depth z on the pulse wave velocity is small.

Figure 6A:
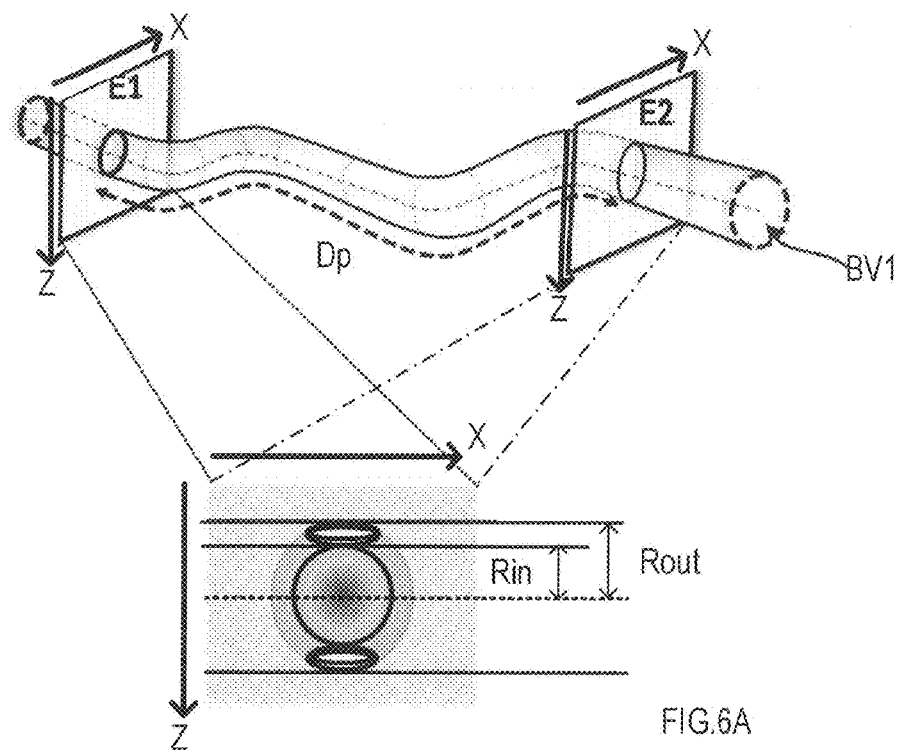
FIGS. 6A-6B are diagrams illustrating a method of calculating a blood flow amount F and blood vessel elasticity E.
Figure 6B:
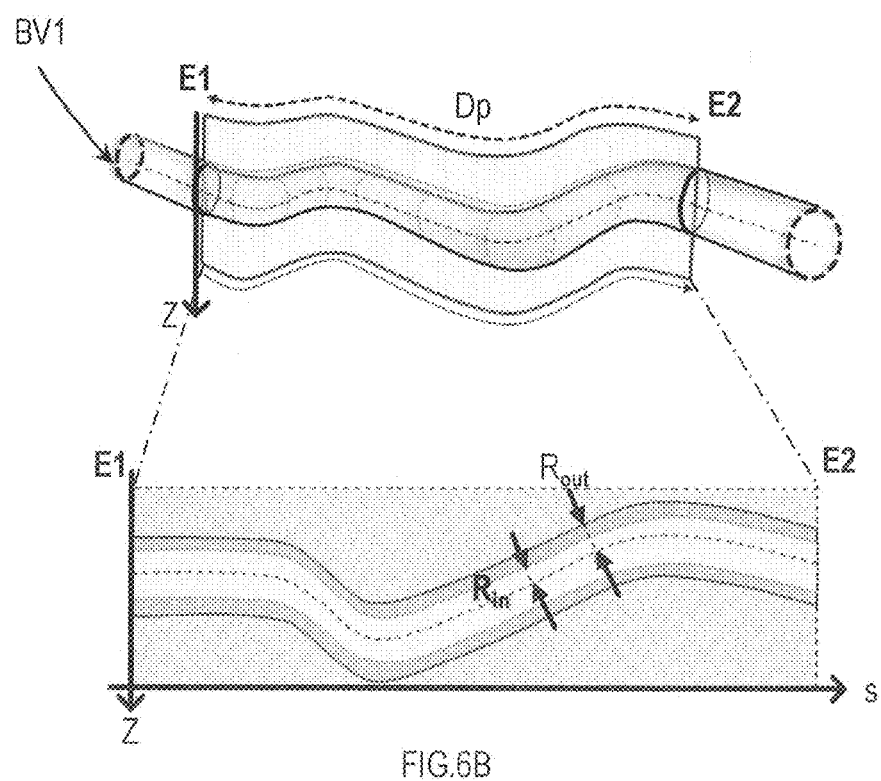

Next, in S140, based on the magnitude of the OCT signal obtained in S40, the outer radius Rout and the inner radius Rin (see FIG. 6A and FIG. 6B) of the blood vessel in the measuring area is calculated. It is to be noted that the inner radius Rin may be calculated with a motion contrast image.

Subsequently, in S150, the blood flow amount F is calculated. Specifically, the pressure change Δp1 (ti) at one end E1 is first calculated with the following formula (3), and the pressure change Δp2 (ti) at the other end E2 is calculated with the following formula (4). The following formulas (3) and (4) are determined from Bramwell-Hill's formula that associates the pulse wave velocity with the pressure change.

[Formula 1]

$$\Delta p_1(t_i) = \frac{\rho\{r_1(t_i)^2 - r_1(t_{i-1})^2\} \times (PWV)^2}{r_1(t_{i-1})^2} \quad (3)$$

$$\Delta p_2(t_i) = \frac{\rho\{r_2(t_i)^2 - r_2(t_{i-1})^2\} \times (PWV)^2}{r_2(t_{i-1})^2} \quad (4)$$

Next, the pressure p1 at one end E1 is calculated with the following formula (5), and the pressure p2 at the other end E2 is calculated with the following formula (6). The pressure pO in the following formulas (5) and (6) is a constant that indicates diastolic blood pressure. Moreover, in the following formula (5), after obtaining the pulse wave of one cycle of pulse, the time at one end E1 is set such that the time at one end E1 when the pulse wave becomes the minimum is set to t0, and becomes time t1, time t2, . . . time ti at every measuring interval Δt. In the following formula (6), the time at the other end E2 is set to time t1, time t2, . . . time ti in the same manner.

The attenuation coefficient of the pulse waves between one end E1 and the other end E2 can be obtained by calculating the ratio of the pulse wave amplitudes (pressure cycle amplitudes). The pressure pO at one end E1 and the pressure pO at the other end E2 are assumed to be identical since the transmission distance Dp is short. If the pressure pO at one end E1 and the pressure pO at other end E2 are assumed to be identical to each other, they are cancelled in the following formula (7).

[Formula 2]

$$p_1(t_i) = p_0 + \Sigma_{n=1}^{i} \Delta p_1(t_n) \quad (5)$$

$$p_2(t_i) = p_0 + \Sigma_{n=1}^{i} \Delta p_2(t_n) \quad (6)$$

Subsequently, the blood flow amount F is calculated with the following formula (7) in which Real [z] is a real part of the complex number z. Moreover, n=2π/Tp is established in which p is the density of blood, i is an imaginary unit, J0 and J1 are Bessel function of order 0 and order 1, respectively. Moreover, a=Rin (ρ·n/μ) ½ is established in which μ is blood fluid viscosity. Moreover, the density ρ and the fluid viscosity μ can be obtained from literature values.

[Formula 3]

$$F(t_i) = \text{Real}\left[\frac{\pi R_{in}^2}{in\rho} \frac{p_2(t_i) - p_1(t_i)}{Dp}\left\{1 - \frac{2\alpha i^{\frac{3}{2}}}{i^3 \alpha^2} \frac{J_1(\alpha i^{\frac{3}{2}})}{J_0(\alpha i^{\frac{3}{2}})}\right\}\right] \quad (2)$$

Furthermore, in S160, based on Moens-Korteweg formula, the blood vessel elasticity (Young's modulus) E is calculated with the following formula (8).

$$E = 2 \times \rho \times Rin \times (PWV)2/(Rout - Rin) \quad (8)$$

When the process of S160 finishes, the process for measuring blood flow is completed.

The blood flow measuring device 1 configured as above comprises the OCT device 2. The OCT device 2 divides light emitted from the light source 11 into reference light and measuring light to emit the measuring light to irradiation points, which are different from each other, on the surface of the sample SP including a blood vessel, and to obtain a two-dimensional tomographic image of the sample SP based on an interference signal in which the reflected light, generated by the measuring light reflected on the sample SP, and the reference light are interfering.

The blood flow measuring device 1 continuously calculates motion contrast signals M (s, z, ti) based on the OCT signals OCT(s, z, ti) at one end E1 and the other end E2 of a measuring area (S40 to S80). The motion contrast signal M (s, z, ti) contains information indicating the two OCT signals calculated between the measuring intervals Δt. Hereinafter, the motion contrast signal M (s, z, ti) at one end E1 is referred to as a first motion contrast signal, and the motion contrast signal M (s, z, ti) at the other end E2 is referred to as a second motion contrast signal.

Moreover, the blood flow measuring device 1 creates pulse wave maps PW (s, z, t) that indicate the chronological change of the first and the second motion contrast signals (S90). Hereinafter, the pulse wave maps PW (s, z, t) based on the first and the second motion contrast signals are referred to as the first and the second pulse wave maps, respectively.

Furthermore, the blood flow measuring device 1 calculates the transmission time Tp (time lag) between the first pulse wave map and the second pulse wave map (S100, S110).

Still furthermore, the blood flow measuring device 1 calculates the transmission distance Dp along the blood vessel BV1 from one end E1 to the other end E2 (S120).

Moreover, the blood flow measuring device 1 calculates the pulse wave velocity PWV of the blood vessel BV1 based on the transmission time Tp and the transmission distance Dp (S130).

As described above, the blood flow measuring device 1 continuously calculates the first and the second motion contrast signals of one end E1 and the other end E2 disposed on the blood vessel BV1, and creates the first and the second pulse wave maps. Accordingly, the blood flow measuring device 1 can obtain the movement of the pulse wave at one end E1 and the other end E2 disposed on the blood vessel BV1.

Moreover, the blood flow measuring device 1 calculates the pulse wave velocity PWV of the blood vessel BV1 based on the transmission time Tp and the transmission distance Dp of the first and the second pulse wave maps. Accordingly, the blood flow measuring device 1 does not need to use the angle formed by the incident direction of the measuring light and the moving direction of the blood inside the blood vessel BV1 in order to measure the pulse wave velocity PWV of the blood vessel BV1. This prevents reduction in the accuracy in the moving speed measured by the blood flow measuring device 1 irrespective of the angle formed by incident direction of the measuring light and moving direction of blood being nearly 90 degrees, and improves the accuracy in speed measurement. Moreover, since the blood flow measuring device 1 can capture the movement of a pulse wave itself, the blood flow measuring device 1 is unlikely to be affected by local turbulent.

Moreover, in the blood flow measuring device 1, the OCT device 2 scans the measuring light on the surface of a sample SP along a blood vessel BV1 that passes through one end E1 and the other end E2.

This allows the blood flow measuring device 1 to increase irradiation positions to be irradiated on the surface of a sample SP along a blood vessel BV1. As the irradiation positions increases on a blood vessel BV1, motion contrast waveforms can be calculated at every narrow interval along the blood vessel BV1, which enables the OCT device 2 to accurately calculate local pulse wave velocity in the blood vessel BV1. Not only the average pulse wave velocity in the measurement range can be known but also, for example, if the blood vessel BV1 branches off on the way, the change in the local pulse wave velocity of before and after the branch can be captured.

Moreover, the blood flow measuring device 1 calculates the inner radius Rin of a blood vessel based on the interference signals obtained by the OCT device 2 (S140). Then, the blood flow measuring device 1 calculates the blood flow amount F of the blood vessel based on the calculated inner radius Rin and the pulse wave velocity PWV (S150). The blood flow measuring device 1 can calculate not only the pulse wave velocity of a blood vessel but also the blood flow amount F of the blood vessel.

Moreover, the blood flow measuring device 1 calculates the outer radius Rout and the inner radius Rin of a blood vessel based on the interference signals obtained by the OCT device 2 (S140). Then, the blood flow measuring device 1, calculates the elasticity E of the blood vessel based on the calculated outer radius Rout and the inner radius Rin and the pulse wave velocity PWV (S160). The blood flow measuring device 1 can calculate not only the pulse wave velocity of a blood vessel but also the elasticity E of the blood vessel.

In the above-described embodiment, the blood flow measuring device 1 may correspond to one example of the speed measuring device of the present disclosure. The OCT device 2 may correspond to one example of the optical coherence tomography of the present disclosure. The motion contrast signal may correspond to one example of the motion contrast of the present disclosure. The program for measuring blood flow 40 may correspond to one example of the speed measuring program the present disclosure.

Moreover, the process of S40 to S80, in particular, the process of S40 and S70 may correspond to one example of the motion contrast calculator and the motion contrast calculation procedure of the present disclosure. The process of S90 may correspond to one example of the waveform creator and the waveform creating procedure of the present disclosure. The process of S100 and S110 may correspond to one example of the time lag calculator and the time lag calculation procedure of the present disclosure. The process of S120 may correspond to one example of the distance calculator and the distance calculation procedure of the present disclosure. The process of S130 may correspond to one example of the speed calculator and the speed calculation procedure of the present disclosure.

Furthermore, the process of S140 may correspond to one example of the inner radius calculator of the present disclosure. The process of S150 may correspond to one example of the blood flow amount calculator the present disclosure. The process of S140 may also correspond to one example of the outer and inner radii calculator of the present disclosure. The process of S160 may correspond to one example of the elasticity calculator of the present disclosure.

Although the above has described one embodiment of the present disclosure, the present disclosure is not limited to the aforementioned embodiment but can be carried out in various ways within the technical scope of the present disclosure.

For example, the aforementioned embodiment shows a case in which Swept Source OCT (SS-OCT) is used. Alternatively, Spectral Domain OCT (SD-OCT) or Time Domain OCT (TD-OCT) may be used.

Moreover, the aforementioned embodiment shows a case in which the OCT device 2 takes two-dimensional tomographic images. Alternatively, the OCT device 2 may take three-dimensional tomographic images.

Furthermore, the aforementioned embodiment shows a case in which, when the blood flow measuring scan finishes, the scanning is automatically switched into the tomographic image scanning. Alternatively, when the blood flow measuring scan finishes, the scanning itself, performed by the scanner 16, may be stopped. In this case, the tomographic image scanning may be restarted, for example, by a user operating on a scanning start button provided to the OCT device 2.

Moreover, the aforementioned embodiment shows a case of single-beam scan. Alternatively, multi-beam scan may be performed.

Figure 7A:
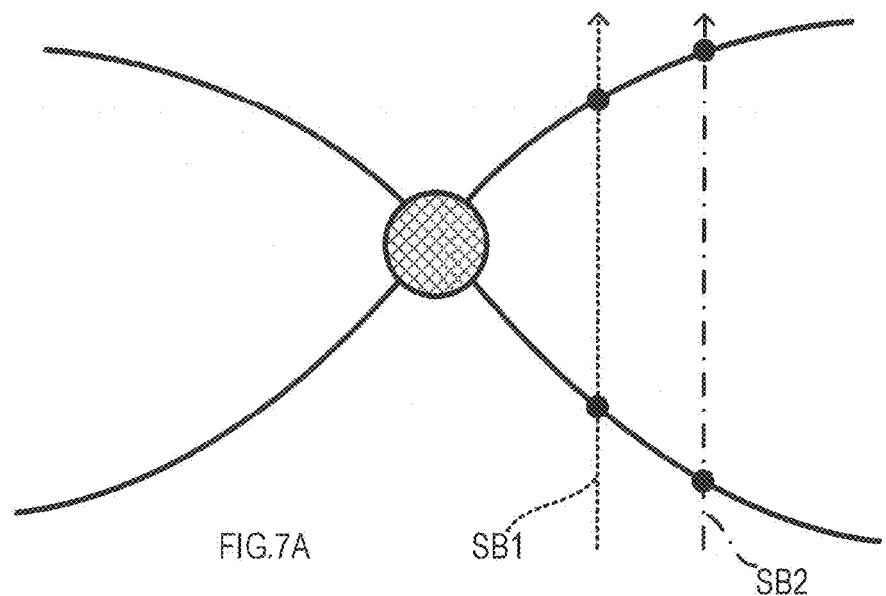
FIGS. 7A-7B are diagrams showing linear scan and circular scan with a dual-beam OCT apparatus.
Figure 7B:
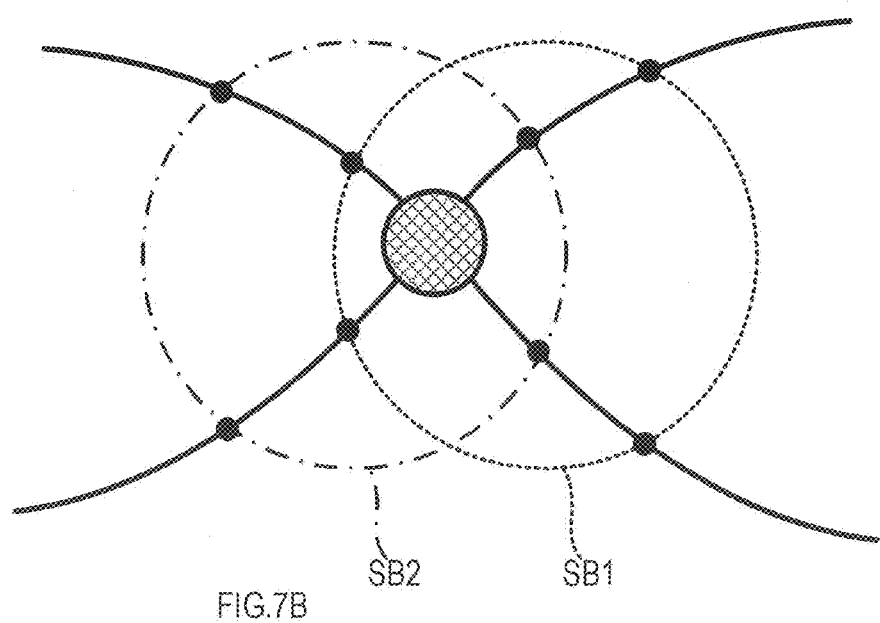

For example, a dual-beam OCT apparatus, configured to be able to simultaneously perform scanning with a first scan beam and a second scan beam, may alternatively performed such that, as shown in FIG. 7A, the first scan beam SB1 and the second scan beam SB2 simultaneously scan different lines, or, as shown in FIG. 7B, may simultaneously scan different circles. This allows obtaining motion contrast signals detected at the same time at two points.

Moreover, the aforementioned embodiment shows an example in which the phase difference of OCT signals is used for motion contrast. However, motion contrast is not limited to this, but may be calculated by a method in which a two-dimensional image can be formed with high sensitivity to the movement of blood (for example, Doppler, in which phase information is used, or Speckle Decorrelation (Speckle Decorrelation)).

Furthermore, the aforementioned embodiment shows an example in which the phase difference of OCT signals is turned into motion contrast signals. Alternatively, the amplitude (magnitude) difference of OCT signals may be turned into motion contrast signals.

Still furthermore, in the aforementioned embodiment, the point where the level of a pulse wave becomes the maximum, and the point where the level of a pulse wave becomes the minimum are signified as the comparison parts. The comparison parts are not limited to these points, but may be other points where some comparable features exist.

Figure 8A:
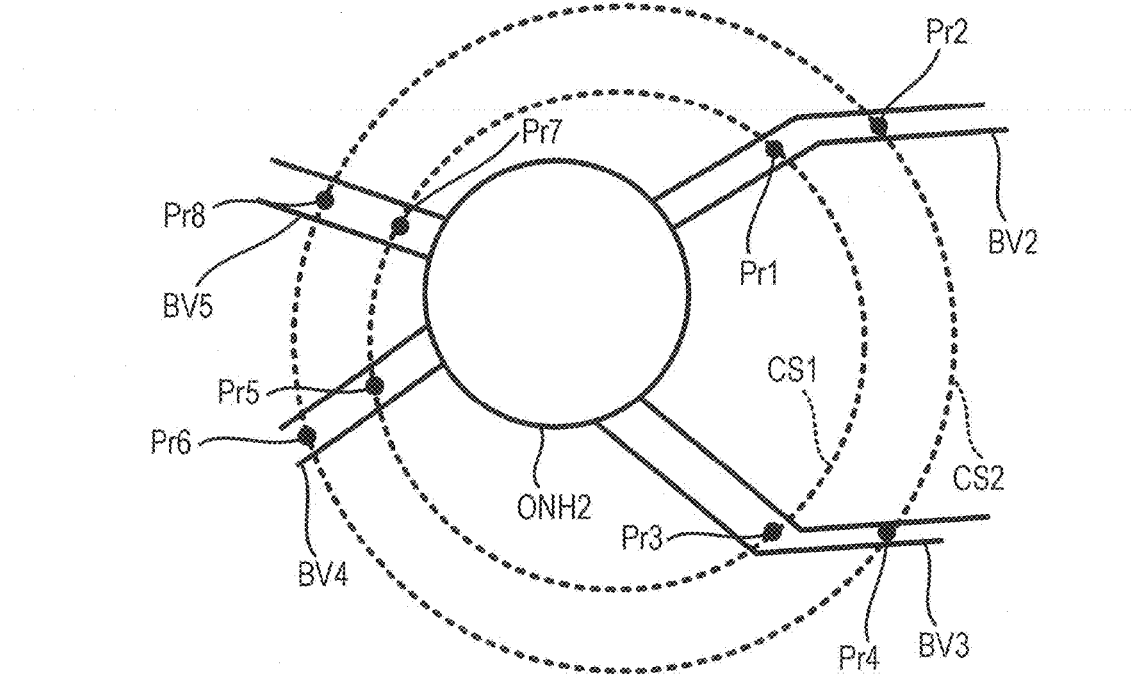
FIGS. 8A-8B are diagrams illustrating a method for measuring the circular scan.

Moreover, the aforementioned embodiment shows an example in which the measuring light scans along a blood vessel. The scanning manner of the measuring light is not limited to this manner, but may be, for example, as shown in FIG. 8A, such that the light beam scans circles that have different diameters to each other. In FIG. 8A, circular scanning CS1, including the optic disc ONH2, and circular scanning CS2, including the optic disc ONH2 and the scan area of the circular scanning CS1, may be performed on the surface of a sample.

In the circular scanning CS1, the measuring light scans in a circular manner so as to intersect with the measuring point Pr1. In the circular scanning CS2, the measuring light scans in a circular manner so as to intersect with the measuring point Pr2 and to include the scan area of the circular scanning CS1.

This allows to calculate the pulse wave velocity of a blood vessel BV2 that passes through both of the measuring point of the circular scanning CS1 and the measuring point of the circular scanning CS2.

Figure 8B:
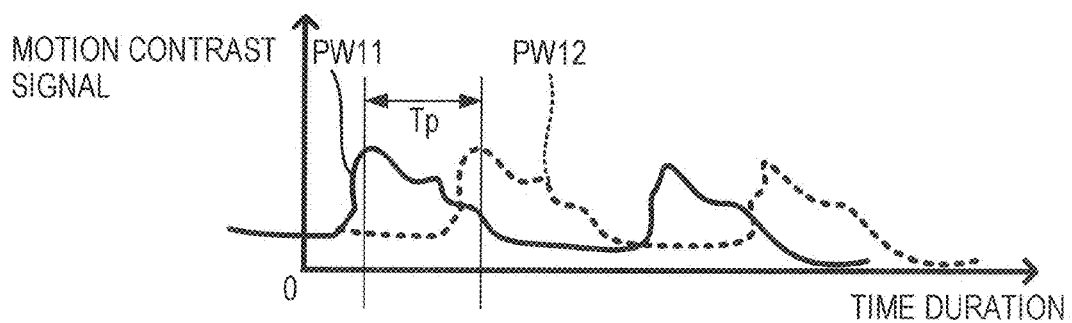

Specifically, the blood vessel BV2 passes through both of the measuring point Pr1 of the circular scanning CS1 and the measuring point Pr2 of the circular scanning CS2. As shown in FIG. 8B, by comparing the pulse wave map PW11 at the measuring point Pr1 and the pulse wave map PW12 at the measuring point Pr2, the transmission time Tp is calculated. From this calculation, the pulse wave velocity of the blood vessel BV2 is calculated.

As described above, by performing the circular scanning CS1 and the circular scanning CS2, motion contrast can be calculated with measuring points in the circle of circular scanning CS1 other than the measuring point Pr1 and measuring points in the circle of the circular scanning CS2 other than the measuring point Pr2.

Specifically, a blood vessel BV3 passes through both of the measuring point Pr3 of the circular scanning CS1 and the measuring point Pr4 of the circular scanning CS2. A blood vessel BV4 passes through both of the measuring point Pr5 of the circular scanning CS1, and the measuring point Pr6 of the circular scanning CS2. A blood vessel BV5 passes both of the measuring point Pr7 of the circular scanning CS1, and the measuring point Pr8 of the circular scanning CS2. Performing the circular scanning CS1 and the circular scanning CS2 allows calculating the pulse wave velocity of the blood vessels BV3, BV4, and BV5.

Moreover, for example, in a case in which the measuring point Pr1 and the measuring point Pr2 are alternately scanned, if the distance between the measuring point Pr1 and the measuring point Pr2 is short, irrespective of the pulse wave velocity being fast, the error in the transmission time Tp becomes large, and the detection accuracy in the pulse wave speed may be decreased. Thus, to calculate the pulse wave velocity, the distance between two measuring points needs to be appropriately set.

Since the number of pulse of human being is substantially 60 times/minute, the cycle To of human pulse is approximately one second. To detect identical comparison part in the identical pulse wave at the measuring point Pr1 and the measuring point Pr2, the transmission time Tp between the measuring point Pr1 and the measuring point Pr2 needs to be smaller than the cycle To. However, this condition can be applied to a case in which the direction of the blood flow is known. For example, in a case in which blood flows from the measuring point Pr1 toward the measuring point Pr2, the comparison part, detected in the measuring point Pr2 from when the comparison part is detected in the measuring point Pr1 until the cycle To passes, can be determined to be from the identical pulse wave.

On the other hand, in a case in which the direction of the blood flow is not clear, $-To/2 < Tp < +To/2$ needs to be met. For example, the comparison part detected at measuring point Pr2 from the time when the comparison part is detected at the measuring point Pr1 and before (To/2) can be determined to be from the identical pulse wave. In this case, blood flow can be determined to be from the measuring point Pr2 toward the measuring point Pr1. Moreover, the comparison part detected at measuring point Pr2 from when the comparison part is detected at the measuring point Pr1 and after (To/2) can be determined to be from the identical pulse wave. In this case, blood flow can be determined to be from the measuring point Pr1 toward the measuring point Pr2.

Accordingly, in a case in which the direction of the blood flow is not clear, to minimize the error of the transmission time Tp as much as possible, the distance between the measuring point Pr1 and the measuring point Pr2 may be set such that the transmission time Tp becomes (To/2)=0.5 [second].

Regarding a capillary in which the blood flow speed is considered to be the slowest in a retina, the blood flow speed of this capillary is substantially 0.3 mm/s. Accordingly, to measure the pulse wave velocity of the capillary of a retina, the distance between the measuring point Pr1 and the measuring point Pr2 may be 0.5 [s]×0.3 [mm/s]=0.15 [mm].

In a case in which blood flow speed (central retinal artery (vein), ciliary artery (vein), and so on) is assumed to be faster than the blood flow speed of this capillary, the distance between the measuring point Pr1 and the measuring point Pr2 should be longer. Accordingly, the distance between the measuring point Pr1 and the measuring point Pr2 should be set so as to be 0.15 mm longer corresponding to the assumed blood flow speed. This prevents, in case of the sample being a retina, an increase of the calculation error of the transmission time Tp, and, therefore, prevents the reduction in the detection accuracy in the pulse wave speed.

Moreover, the aforementioned embodiment shows an example in which the transmission time Tp is calculated by determining the time t in the comparison parts specified in each pulse wave map PW (s, z, t) at two measuring points. However, in a case in which the light beam scans in a circular manner along circles that have different diameters to each other as described above, as shown in FIG. 9, the circular scanning CS1 and the circular scanning CS2 may be switched at every detection of a pulse or a pulse wave.

Specifically, once the pulse PL1 is detected, the circular scanning CS1 is repeated until next pulse PL2 is detected so as to create a pulse wave map PW21 at the measuring point Pr1 from when the pulse PL1 is detected until the pulse PL2 is detected. Once a pulse PL2 is detected, the circular scanning CS2 is repeated until next pulse (not shown) is detected so as to create a pulse wave map PW22 at measuring point Pr2 from when the pulse PL2 is detected until when a next pulse is detected.

Subsequently, the transmission time Tp is calculated based on time Td1, which is from when the pulse PL1 is detected (see time t01) until the when the comparison part of the pulse wave map PW21 is detected (see time t02), and the time Td2, which is from when the pulse PL2 is detected (see time t03) until when the comparison part of the pulse wave map PW22 is detected (see time t04).

Consequently, from when the pulse PL1 is detected until when the pulse PL2 is detected, scanning is performed only to create the pulse wave map PW21. This allows creating a detailed pulse wave map PW21. Similarly, from when the pulse PL2 is detected, scanning is performed only to create the pulse wave map PW22. This allows creating a detailed pulse wave map PW22. Accordingly, a situation, in which comparison parts in the pulse wave map PW21 and the pulse wave map PW22 cannot be detected, can be prevented from taking place. It is to be noted that the pulse wave map PW21 and the pulse wave map PW22 may have captured pulse waves that are different from each other (see the pulse wave maps PW21 and PW22 in FIG. 8). However, under the condition that the blood flow speed does not significantly change at every pulse, in a case in which different pulse waves are captured, the difference between the time Td1 and the time Td2 (Td2−Td1) is substantially equivalent to the difference of the case in which an identical pulse wave is captured in the pulse wave map PW21 and the pulse wave map PW22.

Figure 9:
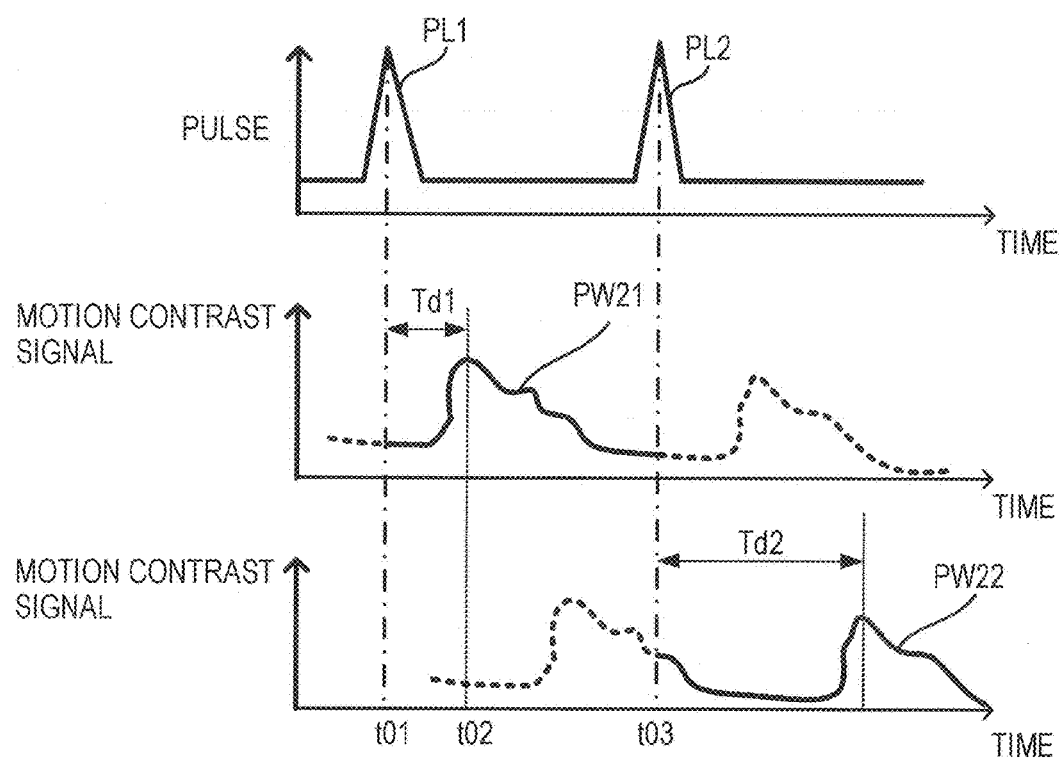
FIG. 9 is a diagram illustrating a method for measuring in synchronization with pulse.

Moreover, FIG. 9 shows an example in which the circular scanning CS1 and the circular scanning CS2 is switched at every detection of a pulse or a pulse wave. Alternatively, the circular scanning CS1 and the circular scanning CS2 may be switched at every preset switch timing. For example, the circular scanning CS1 and the circular scanning CS2 may be switched every time when a switch cycle that is different from the cycle of the pulse or pulse wave passes.

Moreover, FIG. 9 shows an example in which the circular scanning CS1 and the circular scanning CS2 are switched every time when a pulse or a pulse wave is detected. Alternatively, the circular scanning CS1 and the circular scanning CS2 may be switched every time when a plurality of pulses or pulse waves is detected. This enables to obtain a plurality of pulses for each of the circular scanning CS1 and the circular scanning CS2, and, from the time when a pulse or a pulse wave is detected to the time when the comparison part of the pulse wave map is detected, the time Td1 and the time Td2 can be obtained a plurality of times. Thus, by taking the average of a plurality of time Td1, and the average of a plurality of time Td2, the behavior of average pulse may be evaluated, or by calculating the variation in a plurality of time Td1 and a plurality of time Td2, the stability of the pulse may be evaluated.

Furthermore, the aforementioned embodiment shows an example in which blood vessel elasticity (Young's modulus) E is calculated with the formula (8). Alternatively, in a case of fluid with viscosity, blood vessel elasticity (Young's modulus) E may be calculated with the following formula (9).

[Formula 4]

$$E = \frac{2R_{in}\rho(PWV)^2}{h\left(\frac{2+4\mu Tp}{\pi\rho R_{in}^2}\right)} \quad (9)$$

Moreover, the aforementioned embodiment shows an example in which the pulse wave velocity is calculated. Alternatively, the blood flow speed can be evaluated by the blood flow amount and the cross-sectional area of the blood vessel, and the chronological change in the cross-sectional area of the blood vessel can be evaluated.

Moreover, the aforementioned embodiment shows an example in which the arithmetic means of the transmission time Tp (z) and the transmission distance Dp (z), calculated for axially-parallel lines z, are used as the transmission time Tp and the transmission distance Dp, respectively. Alternatively, the transmission time and the transmission distance for a line running in the center of a blood vessel may be used.

Furthermore, the aforementioned embodiment shows an example of two-dimensional scan in which point-like light is directed onto a sample. Alternatively, to increase the speed for obtaining data, a method with linear-light scan may be used.

What is claimed is:

1. A speed measuring device comprising:
an optical coherence tomography that divides light, emitted from a light source, into reference light and measuring light to emit the measuring light to irradiation points, which are different from each other, on a surface of a sample including a blood vessel, and to obtain a tomographic image of the sample based on one or more interference signal(s) in which one or more reflected light(s), obtained from the measuring light reflected on the sample, and the reference light are interfering;
a motion contrast calculator that continuously calculates one or more first motion contrast(s) and one or more second motion contrast(s), among the irradiation points, one irradiation point disposed on the blood vessel being defined as a first irradiation point, and another irradiation point disposed on the blood vessel, passes through the first irradiation point, and being different from the first irradiation point being defined as a second irradiation point, and the one or more first motion contrast(s) being one or more motion contrast(s) calculated based on the one or more interference signal(s) at the first irradiation point, and the one or more second motion contrast(s) being the one or more motion contrast(s) calculated based on the one or more interference signal(s) at the second irradiation point;

a waveform creator that creates, based on a calculation result obtained by the motion contrast calculator, a first motion contrast waveform, indicating chronological change in the one or more first motion contrast(s), and a second motion contrast waveform, indicating a chronological change in the one or more second motion contrast(s);

a time lag calculator that calculates time lag that is temporal lag between the first motion contrast waveform and the second motion contrast waveform created by the waveform creator;

a distance calculator that calculates a blood vessel distance along the blood vessel from the first irradiation point to the second irradiation point; and a speed calculator that calculates, based on the time lag calculated by the time lag calculator and the blood vessel distance calculated by the distance calculator, pulse wave velocity that is velocity of a pulse wave transmitted inside the blood vessel.

2. The speed measuring device according to claim 1, wherein the one or more motion contrast(s) comprise(s) information indicating a phase difference between two interference signals calculated at unidentical time to each other.

3. The speed measuring device according to claim 1, wherein the one or more motion contrast(s) comprise(s) information indicating an amplitude difference between two interference signals calculated at unidentical time to each other.

4. The speed measuring device according to claim 1, wherein the optical coherence tomography scans the measuring light on a surface of the sample along the blood vessel that passes through the first irradiation point and the second irradiation point.

5. The speed measuring device according to claim 1, wherein the optical coherence tomography performs first scan and second scan on a surface of the sample, in the first scan, the measuring light scanning in a circular manner so as to intersect with the first irradiation point, and in the second scan, the measuring light scanning in a circular manner so as to intersect with the second irradiation point and to include a scan area of the first scan.

6. The speed measuring device according to claim 5, wherein the motion contrast calculator calculates the one or more the first motion contrast(s) and the one or more the second motion contrast(s), among the irradiation points, an irradiation point irradiated by the first scan being defined as the first irradiation point, and an irradiation point irradiated by the second scan being defined as the second irradiation point, wherein the time lag calculator calculates the time lag based on a difference between time from when a pulse or a pulse wave is detected until when a preset comparison part of the first motion contrast waveform is detected, and time from when a pulse or a pulse wave is detected until when the comparison part of the second motion contrast waveform is detected.

7. The speed measuring device according to claim 1, further comprising:

an inner radius calculator that calculates an inner radius of the blood vessel based on the one or more interference signal(s) obtained by the optical coherence tomography; and a blood flow amount calculator that calculates a blood flow amount of the blood vessel based on the inner radius calculated by the inner radius calculator and the pulse wave velocity calculated by the speed calculator.

8. The speed measuring device according to claim 1, further comprising:

an outer and inner radii calculator that calculates an outer radius and an inner radius of the blood vessel based on the one or more interference signal(s) obtained by the optical coherence tomography; and an elasticity calculator that calculates blood vessel elasticity of the blood vessel based on the outer radius and the inner radius calculated by the outer and inner radii calculator and the pulse wave velocity calculated by the speed calculator.

9. The speed measuring device according to claim 1, wherein, if the sample is an eye, the positions of the first irradiation point and the second irradiation point are set such that the blood vessel distance is extended by 0.15 mm.

10. A non-transitory tangible recording medium that stores speed measuring program to make a computer function as each means of a speed measuring device that comprises:

an optical coherence tomography that divides light, emitted from a light source, into reference light and measuring light to emit the measuring light to irradiation points, which are different from each other, on a surface of a sample including a blood vessel, and to obtain a tomographic image of the sample based on one or more interference signal(s) in which one or more reflected light(s), obtained from the measuring light reflected on the sample, and the reference light are interfering;

a motion contrast calculator that continuously calculates one or more first motion contrast(s) and one or more second motion contrast(s), among the irradiation points, one irradiation point disposed on the blood vessel being defined as a first irradiation point, and another irradiation point disposed on the blood vessel, passing through the first irradiation point, and being different from the first irradiation point being defined as a second irradiation point, and the one or more first motion contrast(s) being one or more motion contrast(s) calculated based on the one or more interference signal(s) at the first irradiation point, and the one or more second motion contrast(s) being the one or more motion contrast(s) calculated based on the one or more interference signal(s) at the second irradiation point;

a waveform creator that creates, based on a calculation result obtained by the motion contrast calculator, a first motion contrast waveform, indicating chronological change in the one or more first motion contrast(s), and a second motion contrast waveform, indicating a chronological change in the one or more second motion contrast(s);

a time lag calculator that calculates time lag that is temporal lag between the first motion contrast waveform and the second motion contrast waveform created by the waveform creator;

a distance calculator that calculates a blood vessel distance along the blood vessel from the first irradiation point to the second irradiation point; and a speed calculator that calculates, based on the time lag calculated by the time lag calculator and the blood vessel distance calculated by the distance calculator, pulse wave velocity that is velocity of a pulse wave transmitted inside the blood vessel.

11. A method for measuring speed that uses an optical coherence tomography that divides light, emitted from a light source, into reference light and measuring light to emit the measuring light to irradiation points, which are different from each other, on a surface of a sample including a blood vessel, and to obtain a tomographic image of the sample based on one or more interference signal(s) in which one or more reflected light(s), obtained from the measuring light reflected on the sample, and the reference light are interfering, the method comprising:

a motion contrast calculating procedure wherein one or more first motion contrast(s) and one or more second motion contrast(s) are continuously calculated, among the irradiation points, one irradiation point disposed on the blood vessel being defined as a first irradiation point, and another irradiation point being disposed on the blood vessel, passing through the first irradiation point, and being different from the first irradiation point being defined as a second irradiation point, and the one or more first motion contrast(s) being one or more motion contrast(s) calculated based on the one or more interference signal(s) at the first irradiation point, and the one or more second motion contrast(s) being the one or more motion contrast(s) calculated based on the one or more interference signal(s) at the second irradiation point;

a waveform creating procedure wherein, based on a calculation result obtained by the motion contrast calculating procedure, a first motion contrast waveform, indicating chronological change in the one or more first motion contrast(s), and a second motion contrast waveform, indicating a chronological change in the one or more second motion contrast(s) are created;

a time lag calculating procedure wherein time lag that is temporal lag between the first motion contrast waveform and the second motion contrast waveform created by the waveform creating procedure are calculated;

a distance calculating procedure wherein a blood vessel distance along the blood vessel from the first irradiation point to the second irradiation point is calculated; and a speed calculating procedure wherein, based on the time lag calculated by the time lag calculating procedure and the blood vessel distance calculated by the distance calculating procedure, pulse wave velocity that is velocity of a pulse wave transmitted inside the blood vessel is calculated.

* * * * *

UNITED STATES PATENT AND TRADEMARK OFFICE
CERTIFICATE OF CORRECTION

PATENT NO. : 10,154,784 B2
APPLICATION NO. : 15/176825
DATED : December 18, 2018
INVENTOR(S) : Franck E. M. Jaillon et al.

It is certified that error appears in the above-identified patent and that said Letters Patent is hereby corrected as shown below:

In the Specification

<u>In the Equations</u>

In Column 8, Line 28, please replace Equation (2) with the following:

$\Delta \phi = 4\pi \times vz \times \Delta t / \lambda$

In Column 10, Line 33, please replace [Formula 2] with the following:

$$p_1(t_i) = p_0 + \sum_{n=1}^{i} \Delta p_1(t_n) \quad \cdots (5)$$

$$p_2(t_i) = p_0 + \sum_{n=1}^{i} \Delta p_2(t_n) \quad \cdots (6)$$

Signed and Sealed this
Thirtieth Day of April, 2019

Andrei Iancu
*Director of the United States Patent and Trademark Office*